United States Patent [19]
Bowman

[11] Patent Number: 5,797,398
[45] Date of Patent: Aug. 25, 1998

[54] METHOD AND APPARATUS FOR MEASURING CONTINUOUS BLOOD FLOW AT LOW POWER

[75] Inventor: Harry Frederick Bowman, Needham, Mass.

[73] Assignee: Thermal Technologies, Inc., Cambridge, Mass.

[21] Appl. No.: 106,068

[22] Filed: Aug. 13, 1993

[51] Int. Cl.$^6$ ..................................................... A61B 5/00
[52] U.S. Cl. ........................... 128/692; 128/713; 128/736
[58] Field of Search .............................. 128/668, 691–4, 128/713, 736

[56] References Cited

U.S. PATENT DOCUMENTS

| | | |
|---|---|---|
| 3,359,974 | 12/1967 | Khalil . |
| 4,059,982 | 11/1977 | Bowman . |
| 4,105,022 | 8/1978 | Antoshkion et al. . |
| 4,217,910 | 8/1980 | Khalil ........................... 128/670 |
| 4,230,126 | 10/1980 | Elings ........................... 128/692 |
| 4,236,527 | 12/1980 | Newbower et al. . |
| 4,354,504 | 10/1982 | Bro . |
| 4,507,974 | 4/1985 | Yelderman . |
| 4,595,015 | 6/1986 | Jansen ........................... 128/692 |
| 4,685,470 | 8/1987 | Sekii et al. . |
| 4,730,623 | 3/1988 | Lee ................................ 128/692 |
| 4,785,823 | 11/1988 | Eggers et al. . |
| 4,901,734 | 2/1990 | Griffin et al. . |
| 4,979,514 | 12/1990 | Sekii et al. . |
| 5,000,190 | 3/1991 | Petre . |
| 5,009,234 | 4/1991 | Art ................................ 128/692 |
| 5,080,106 | 1/1992 | Sekii et al. ................... 128/692 |
| 5,146,414 | 9/1992 | McKown et al. ............. 364/510 |
| 5,174,299 | 12/1992 | Nelson ......................... 128/692 |
| 5,285,796 | 2/1994 | Hughes ........................ 128/713 |
| 5,305,760 | 4/1994 | McKown et al. ............. 128/692 |
| 5,383,468 | 1/1995 | Nakayama et al. .......... 128/713 |

FOREIGN PATENT DOCUMENTS

WO A
91/17703  11/1991  WIPO .

OTHER PUBLICATIONS

Delaunois, "Thermal Method for Continuous Blood–Velocity Measurements in Large Blood Vessels, and Cardiac–Output Determination", *Medical and Biological Engineering*, Mar. 1973, vol. 11, No. 2, pp. 201–205.

Edwards Critical–Care Division Vigiliance Monitor Technical Manual Jan. 1994, Baxter Healthcare Corporation, Copyright 1993 and 1994, pp. 2–15, 2–16, cover page and two copyright pages.

Khalial, "Determinations of Cardiac Output in Man by a New Method Based on Thermodilution", *The Lancet*, Preliminary Communications, Jun. 22, 1963, pp. 1352–1354.

Philip, et al., "Continuous Thermal Measurement of Cardiac Output", *IEEE Transactions on Biomedical Engineering*, vol. BME–31, No. 5, May, 1984, pp. 393–400.

"The Omega Complete Flow and Level Measurement Handbook and Encyclopedia"; Omega Engineering, Inc. (1989), pp. D–3 through D–6.

Forrester, James S., et al., "Thermodilution cardiac output determination with a single flow–directed catheter", *American Heart Journal*, Clinical Communications, vol. 83, No. 3, (Mar. 1972), pp. 306–311.

Normann, R.A., et al., "A Continuous Cardiac Output Computer Based on Thermodilution Principles", *Annals of Biomedical Engineering*, vol. 17, (1989), pp. 61–73.

Taylor, Bruce C., et al., "Understanding Techniques For Measuring Cardiac Output", *Biomedical Instrumentation & Technology*, May/Jun. 1990, pp. 187–197.

*Primary Examiner*—Robert L. Nasser
*Attorney, Agent, or Firm*—Ernest V. Linek

[57] ABSTRACT

A technique for determining blood flow in a living body by changing the thermal energy level by a predetermined amount at a site in a blood flow path and detecting temperatures at locations upstream and downstream of the site. The temperature difference at such locations is determined and the blood flow is calculated as a function of the change in energy level and of the temperature differences measured prior to and following the change in energy level.

53 Claims, 6 Drawing Sheets

PROCESS II

PROCESS III

PROCESS IV $F_3 \propto \frac{1}{T} \int P_3(t)/\Delta T_3(t)\, dt =$ CARDIAC OUTPUT

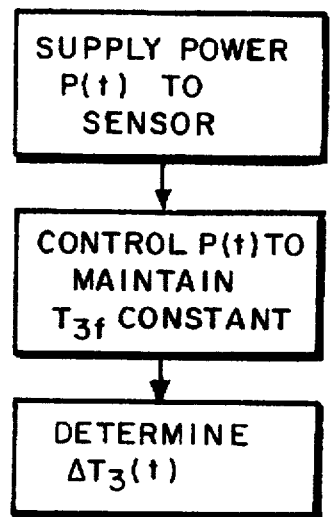
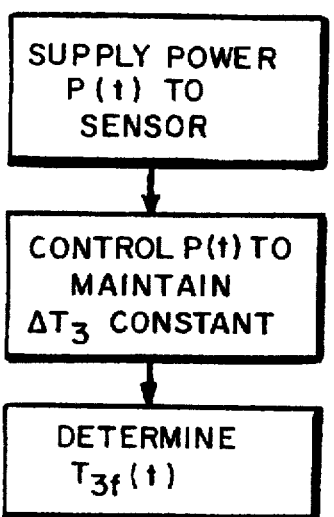
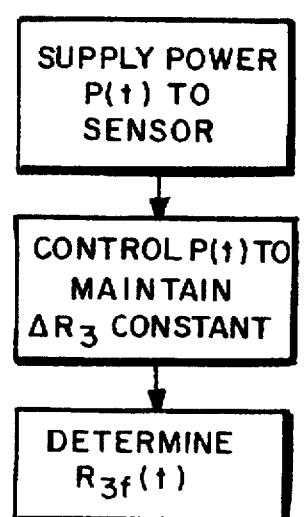
FIG.8A    FIG.8B    FIG.8C
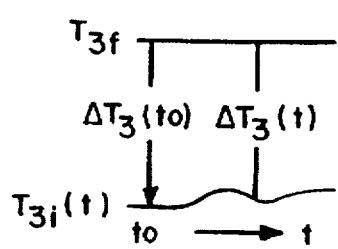
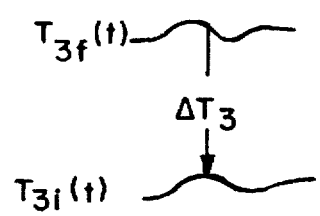
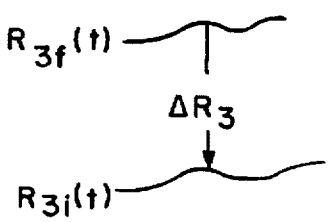
FIG.9A    FIG.9B    FIG.9C
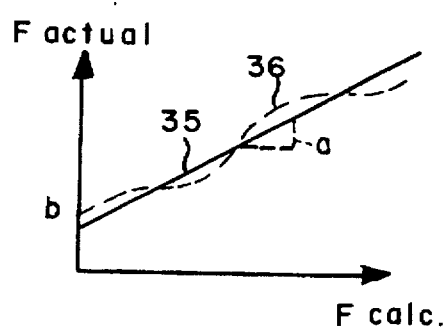
FIG.10

METHOD AND APPARATUS FOR MEASURING CONTINUOUS BLOOD FLOW AT LOW POWER

INTRODUCTION

This invention relates generally to techniques for measuring blood flow in a body and, more particularly, to the use preferably of one or more temperature sensors for measuring thermal energy changes in the blood flowing through the heart and to the use of unique data processing techniques in response thereto for determining cardiac output.

BACKGROUND OF THE INVENTION

While the invention can be used generally to measure blood flow at various locations in a body, it is particularly useful in measuring blood flow in the heart so as to permit the measurement of cardiac output. Many techniques for measuring cardiac output have been suggested in the art. Exemplary thermodilution techniques described in the technical and patent literature include: "A Continuous Cardiac Output Computer Based On Thermodilution Principles", Normann et al., Annals of Biomedical Engineering, Vol. 17, 1989; "Thermodilution Cardiac Output Determination With A single Flow-Directed Catheter", Forrester, et al., American Heart Journal, Vol. 83, No. 3, 1972; "Understanding Techniques for Measuring Cardiac Output", Taylor, et al., Biomedical Instrumentation & Technology, May/June 1990; U.S. Pat. No. 4,507,974 of M. L. Yelderman, issued Apr. 2, 1985; U.S. Pat. No. 4,785,823, of Eggers et al., issued on Nov. 22, 1988; and U.S. Pat. No. 5,000,190, of John H. Petre, issued on Mar. 19, 1991.

A principal limitation in the quanification of cardiac output is the existence of thermal fluctuations inherent in the bloodstream. Previous methods work with those fluctuations while observing the effects of an input signal to calculate cardiac output. The invention described herein uses a differential measurement technique to substantially eliminate the effect of the thermal fluctuations, permitting the use of a minimal thermal input signal, which allows frequent or continuous measurements.

It is desirable to obtain accurate cardiac output measurements in an effectively continuous manner, i.e., several times a minute, so that a diagnosis can be achieved more rapidly and so that rapid changes in a patient's condition can be monitored on a more continuous basis than is possible using current techniques. Moreover, it is desirable to obtain instantaneous measurements of the cardiac output on a beat-to-beat basis to evaluate the relative changes which occur from beat to beat, as well as to determine the presence of regurgitation.

BRIEF SUMMARY OF THE INVENTION

In accordance with general principal of the invention, blood flow and/or cardiac output is determined rapidly, using a technique by which an indicator substance, or agent, is introduced into the bloodstream between a pair of detectors. The detectors are sensitive to a parameter functionally related to the concentration or magnitude in the bloodstream of the selected indicator agent. The detectors are positioned apart by a distance functionally sufficient to allow a measurement to be made of the differential value of the selected parameter as it exists from time-to-time between the two detectors. The indicator agent, for example, may be a substance to change the pH of the blood, a fluid bolus carrying thermal energy, or a substance to change a selected characteristic of the blood, or the direct introduction of thermal energy, or the like.

A determination is made of the difference in the values of the selected blood parameter as it exists at the two detectors, prior to the introduction of indicator agent (i.e., the first differential value). The selected indicator agent is then introduced in a predetermined magnitude. Then again a determination is made of the difference in values of the selected parameter as it exists at the locations of the two detectors (i.e., the second differential value).

Blood flow or cardiac output, depending on the specific location of the detectors, can then be determined as a function of the difference between the first differential value and the second differential value. Because the ultimate measurement of blood flow or cardiac output is based on the difference of the differences, the system operates effectively with the introduction of the indicator agent in a very low magnitude. In turn, this allows measurements to be made rapidly so that effectively continuous measurements are obtained.

In accordance with a preferred embodiment of the invention, for example, cardiac output can be determined rapidly and with low levels of thermal energy input. To achieve such operation, in a preferred embodiment, the technique of the invention uses a pair of temperature sensors positioned at two selected locations within a catheter which has been inserted into the path of the blood flowing through the heart of a living body. The sensors detect the temperature difference between the two locations. Depending on the location of the temperature sensors in the circulatory system, the measured temperature difference varies over time. It has been observed that when the temperature sensors are placed within the heart, e.g., so that one sensor lies in the vena cava, for example, and the second in the right ventricle or pulmonary artery, the temperature difference varies in a synchronous manner with the respiratory cycle.

Thus, in the preferred embodiment of the invention the temperature difference over at least one respiratory cycle is measured and averaged to provide an average temperature difference. The averaging, or integrating, action effectively eliminates, as a confounding factor in the determination of cardiac output, the effect of instantaneous blood temperature fluctuations, such as cyclical, respiratory-induced fluctuations.

To make such determinations, an average temperature difference is first calculated over a time period of at least one respiratory cycle in which no thermal energy is introduced into the blood flow path. Thermal energy of a predetermined and relatively low magnitude is then introduced into the blood flow path to produce a heating action therein at a location between the two temperature sensors. Once the temperature rise induced by the heating stabilizes, the average temperature difference between the two locations is again calculated from temperature difference measurements over a time period of at least one respiratory cycle at the higher temperature level. The difference between the average temperature differences which occurs when the thermal energy is turned on, referred to as the rising temperature change, is determined. The difference between the average temperature differences which occurs when the thermal energy is turned off, referred to as the falling temperature change, is similarly determined. The cardiac output is calculated as a function of the thermal energy input and the rising and falling temperature changes. Because a relatively low level of thermal energy is used in making measurements, the overall sequence of determinations can be safely repeated multiple times per minute, for example, so that an effectively continuous, or quasi-continuous, determination of cardiac output is obtained.

In accordance with a further embodiment of the invention, a temperature sensor that also acts as a source of thermal energy, e.g., a thermistor, is positioned at a third location in the cardiac blood flow path. Power is supplied to the sensor sufficient to elevate the temperature of the sensor from a first temperature level to a second temperature level. In one embodiment of the invention, the temperature of the sensor is changed from the first to the second level and is maintained constant at said second level by varying the power that is supplied thereto. Such varying power is proportional to the instantaneous flow velocity and, hence, assuming a constant flow area, is proportional to the instantaneous cardiac output. Measurement of the sensor heating power and the temperature increment at the sensor can thus be used to continuously effect a determination of the instantaneous cardiac output. Further, for example, when the sensor is placed downstream at the outlet of one of the heart chambers, the variation in flow output over the cardiac cycle can be analyzed to provide an indication of the regurgitation characteristics of the heart outlet valve over the cardiac cycle. Moreover, such instantaneous cardiac output determination can be further refined to compensate for fluctuations in the temperature of the blood flowing through the heart by measuring the instantaneous temperature of the blood with another temperature sensor at a nearby location and appropriately taking into account such temperature variations when determining the cardiac output.

In another application, both the continuous cardiac output determinations and the instantaneous cardiac output determinations, as described above, can be combined. Thus, three temperature sensors and a source of thermal energy can all be used in combination to simultaneously provide an accurate and effectively continuous determination of time-averaged cardiac output, and a determination of instantaneous cardiac output at each instant of the cardiac cycle. In still another application, two temperature sensors and a source of thermal energy can be used in an appropriate sequence to provide the averaged cardiac output determination and the instantaneous cardiac output determination.

DESCRIPTION OF THE INVENTION

The invention can be described in more detail with the help of the accompanying drawings wherein FIG. 1 shows a simplified diagrammatic view of a human heart;

FIGS. 8A, 8B, and 8C show flow charts depicting modes of operating the process of the invention;

FIGS. 9A, 9B, and 9C show graphs of parameter relationships used in the invention; and FIG. 10 shows a graph useful for calibrating the flow values for a catheter used in the invention.

Figure 1:
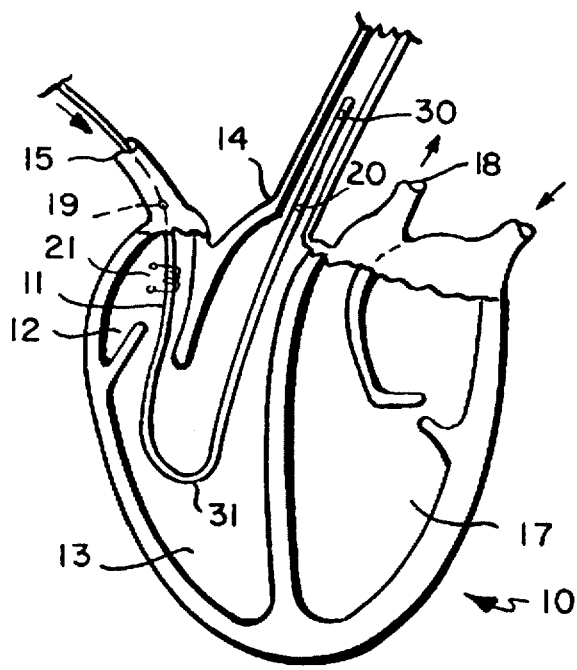

As can be seen in FIG. 1, which represents a human heart 10 in a much simplified diagrammatic form, a flexible catheter 11 is inserted through the veins into the right atrium, or auricle, 12 of the heart and, thence, through the right ventricle 13 until the end of the catheter resides in or near the exit, or pulmonary, artery 14 which leads to the lungs. As is well known, blood flows (as represented by the arrows) from the input vein 15, i.e., the vena cava, into the right atrium and right ventricle and thence outwardly to the lungs and subsequently returns from the lungs into the left atrium 16, through the left ventricle 17 and thence outwardly into the aorta 18.

In accordance with the embodiment of the invention, shown with reference to FIG. 1, temperature sensors, e.g., thermistors, are carried by the catheter so that, when inserted as shown in FIG. 1, a first sensor 19 is positioned at a location within the vena cava 15 or right atrium 12 and a second sensor 20 is positioned at a location in or near the pulmonary artery 14.

Figure 2:
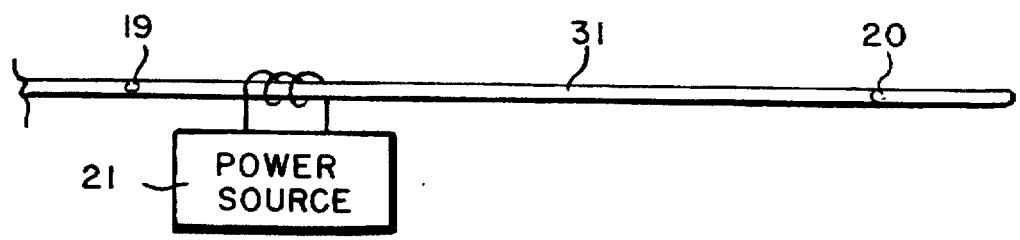
FIG. 2 shows a simplified diagrammatic view of a catheter useful in the invention.

For simplicity, the flexible catheter 11 is depicted in FIG. 2 in an extended condition with temperature sensors 19 and 20 at two different locations for measuring temperatures $T_1$ and $T_2$, respectively. A power source 21 of thermal energy which is borne, or carried, by the catheter 11 is positioned in the right atrium at a location between sensors 19 and 20. In a particular embodiment, the catheter-borne source is, for example, a coil of resistive wire placed on or embedded in the surface of catheter 11, to which an AC or a DC voltage (not shown) at a controllable level is supplied so as to generate thermal energy, i.e. heat. The magnitude of the thermal energy can be suitably controlled to insert a predetermined amount of thermal energy at a selected time, which thermal energy is transferred to the blood flowing through the heart so as to raise its temperature. The energy source is positioned at a sufficient distance from the sensor 19 that the latter is effectively thermally isolated from the site of the thermal energy source.

While the locations of the sensors 19 and 20 and the energy source 21 can be as shown in FIG. 1, alternative locations can also be used. Thus, the sensor 19 can be positioned in the vena cava 15, while the energy source 21 is located in the right atrium 12 and the sensor 20 in either the right atrium or the right ventricle. Moreover, if sensor 19 is positioned in the vena cava 15, the entire energy source 21, which is normally elongated, need not be located in the right atrium and can have a portion thereof in the vena cava and a portion thereof in the right atrium. Such source should preferably be at least partially located in the right atrium. Further, sensor 20 may be positioned in the right ventricle near the pulmonary artery 14 or may be located in the pulmonary artery itself at or near the right ventricle.

The temperatures $T_1$ and $T_2$ at locations 19 and 20 upstream and downstream, respectively, from the thermal energy source 21 are monitored and processed appropriately by a digital microprocessor. In accordance with the invention, the instantaneous temperatures are obtained as the outputs $T_1(t)$ and $T_2(t)$ of the temperature sensors 19 and 20, respectively. The outputs are connected to a differential amplifier to generate an analog signal which is proportional to the temperature difference $\Delta T(t) = T_1(t) - T_2(t)$ between them. The temperature difference signal ΔT(t) is digitized and sampled at selected time intervals by an analog-to-digital/sampling circuit. The digitized sampled temperature difference values and the known thermal energy values are supplied to a digital microprocessor which then suitably processes the data to provide the desired cardiac output information. The processing stages used in the host microprocessor are implemented by suitable programming of the microprocessor and are discussed below with the help of FIGS. 3–6.

The source 21 of thermal energy is alternately turned on and off. If it is assumed that thermal stability is reached after each change and that there is a substantially constant rate of blood flow, a stable temperature difference can be measured in each case. The quantity of blood flowing past the thermal energy source, i.e., the cardiac output, can be derived from such temperature difference measurements. However, such derivation is complicated by two factors which may affect the measurement of blood flow. First, the rate of blood flow through the heart is not substantially constant but surges with each heart contraction. Second, the temperature of the blood flowing through the heart is not constant but varies with each respiratory (breathing) cycle. In a preferred embodiment, the processing of the data takes such factors into account, as discussed below.

Figure 3:
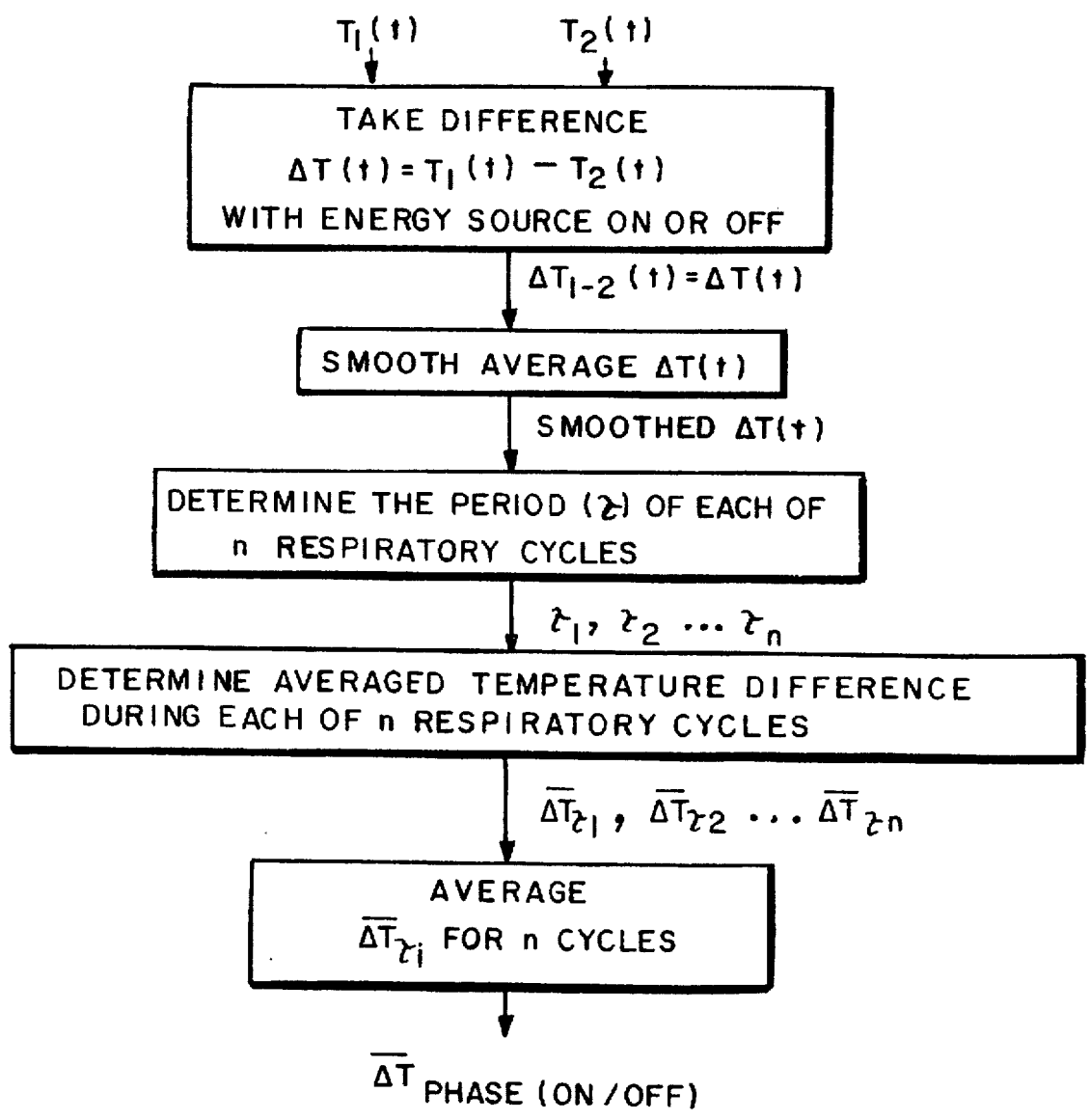
FIG. 3 shows a flow chart depicting steps in a process used in the invention.
Figure 4:
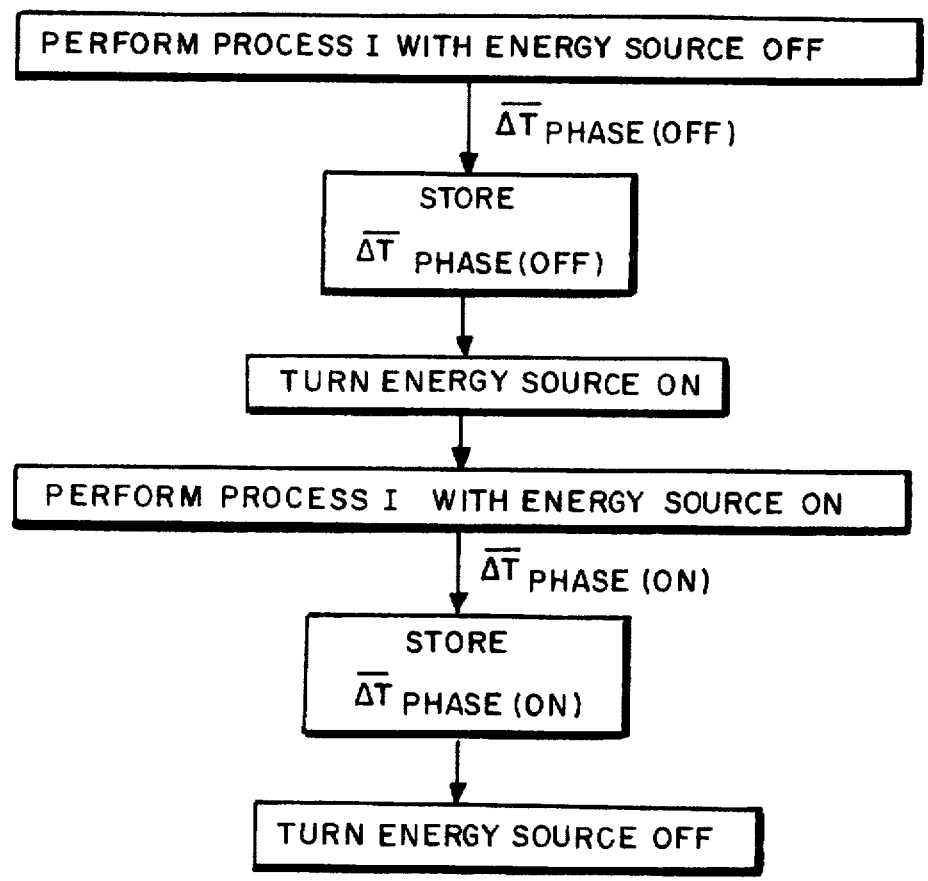
FIG. 4 shows a flow chart depicting further steps in process used in the invention.
Figure 5:
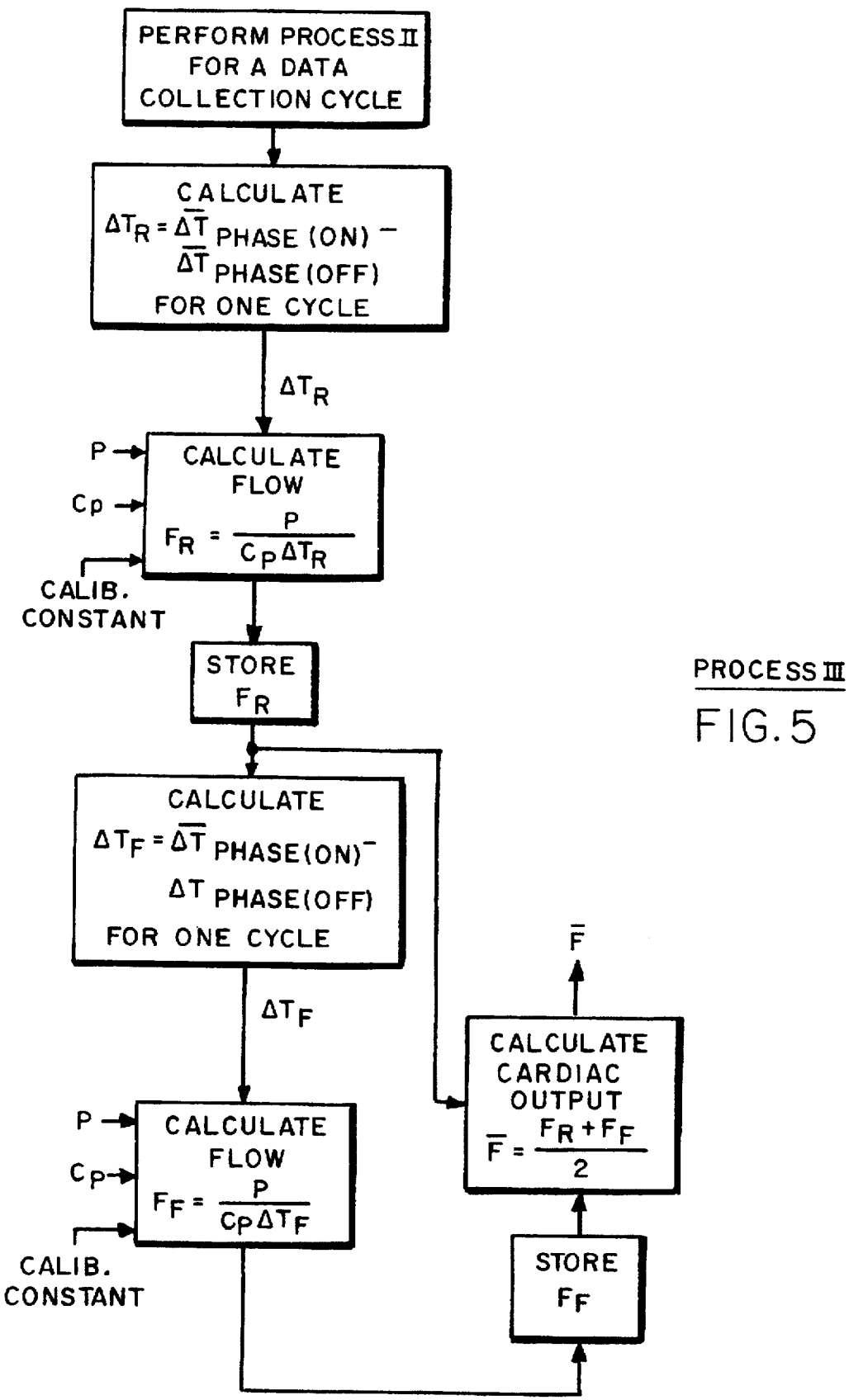
FIG. 5 shows a flow chart depicting still further steps in process of the invention.

The process for determining cardiac output is performed in a microprocessor 2 which in a first embodiment is programmed to respond to the temperatures sensed at $T_1$ and $T_2$ and to perform the steps depicted in accordance with the flow charts shown in FIGS. 3–5. From a knowledge of such flow charts, it would be well within the skill of those in the art to appropriately program any suitable and known digital microprocessor, such as a personal computer, to perform the steps shown.

Figure 3A:
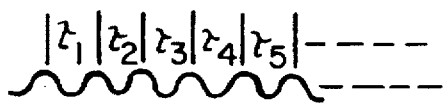
FIG. 3A shows a smooth temperature difference curve obtained in the process depicted in FIG. 3.

FIG. 3 depicts a basic process, identified as Process I, which is used in the overall processing of temperature data for determining cardiac output, as subsequently depicted in FIGS. 4 and 5. In the basic process shown in FIG. 3, a temperature difference as a function of time ΔT(t) is determined by a differential amplifier which responds to $T_1(t)$ and $T_2(t)$. Such differences may be effectively smoothed, or filtered, to produce a smooth temperature difference curve, as shown in FIG. 3A, which varies as a function of time in a cyclic manner which depends principally on the respiratory cycle of the person whose cardiac output is being determined.

The periods $\tau_1, \tau_2 \ldots \tau_n$ for each respiratory cycle are determined over n cycles. A characteristic of the temperature difference at each cycle is determined. For example, such characteristic preferably is the averaged temperature difference during each cycle ($\Delta T_{r1}, \Delta T_{r2} \ldots \Delta T_{r2} \ldots \Delta T_{rn}$).

(Alternatively, for example, the peak temperature differences may be the determined characteristic.) These averaged temperature differences ($\Delta T_m$) are added for the n cycles involved and are divided by n to determine an averaged temperature difference per cycle ($\Delta T_m$). The use of Process I is depicted in the process steps shown in FIG. 4, identified as Process II.

As seen therein, the steps of Process I are first performed when the source 21 of thermal energy (i.e., a heater) is turned off and the average $\overline{\Delta T}_{off}$ value per cycle is determined and suitably stored. The sampling time at which such determination is made is depicted in FIG. 6 as the sample time period S1.

Figure 6:
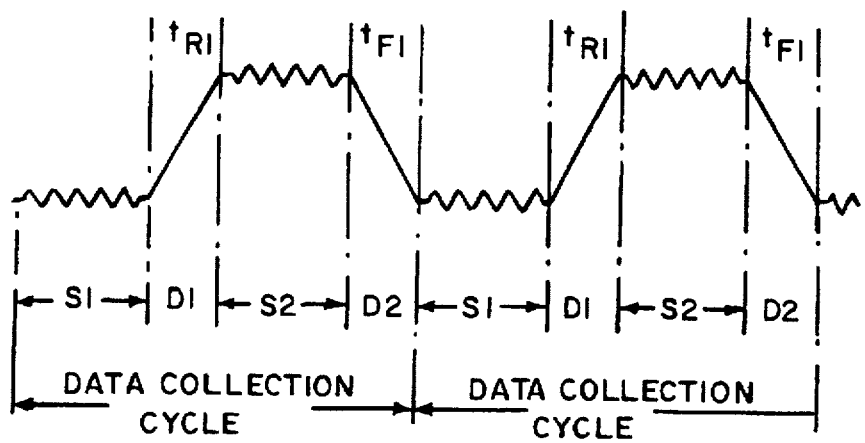
FIG. 6 shows a graph depicting a temperature/time relation used in the invention.

The heater 21 is then turned on for a specific time period to supply a known amount of power P to the blood flowing through the heart and, accordingly, the temperature of the blood flowing past the heater rises and the temperature difference ΔT(t) rises over a transition, or delay, rise time period, $t_{R1}$, shown in FIG. 6 and designated as D1, after which the temperature difference generally stabilizes over a second sample time period S2. As seen in FIG. 4, after the heater 21 is turned on and the temperature has stabilized, Process I is performed, again over n cycles, e.g., over the time period S2, and the averaged temperature difference $\overline{\Delta T}_{on}$ is determined with the heater turned on and is suitably stored. The heater is then turned off and the temperature falls over a transition, or delay, fall time period $t_{F1}$, shown in FIG. 6 and designated as D2, generally to its former value.

Cardiac output is calculated using the averaged temperature differences when the energy is off and the averaged temperature differences when the energy is on, by the relationship:

$$F = \frac{P}{C_p(\overline{\Delta T}_{on} - \overline{\Delta T}_{off})}$$

where:

F=Flow

P=Power $C_p$=heat capacitance $\overline{\Delta T}_{on}$=average temperature for power on $\overline{\Delta T}_{off}$=average temperature for power off As seen in FIG. 5, the steps of Process II are repeated indefinitely for N data collection cycles, a data collection cycle being designated as including the time periods S1, D1, S2, and D2, as shown in FIG. 6. For each data collection cycle the rise time temperature difference ΔTR between the averaged temperature difference $\overline{\Delta T}_{on}$ at S2 and the averaged temperature difference $\overline{\Delta T}_{off}$ at S1 and the fall time temperature difference $\Delta T_F$ between the averaged temperature difference $\overline{\Delta T}_{off}$ at S1 and the averaged temperature difference $\overline{\Delta T}_{on}$ at S2 are determined.

The flow, $F_R$, is calculated for each data collection cycle from the known amount of power P introduced into the blood flow stream by the energy source, or heater 21, from the known heat capacitance of blood, $C_P$ and from the difference in the averaged temperature differences $\overline{\Delta T}_{on}$ and $\overline{\Delta T}_{off}$ which occurs over the data collection cycle S1+D1+S2 in accordance with the following relationship:

$$F_R = \frac{P}{C_p(\overline{\Delta T}_{on} - \overline{\Delta T}_{off})}$$

In a similar manner, the flow $F_F$ is calculated from P, $C_P$ and the difference in the averaged temperature differences $\Delta T_{on}$ and $\Delta T_{off}$ which occurs over the later portion of the data collection cycle S1+D1+S2 in accordance with the following relationship:

$$F_F = \frac{P}{C_p(\overline{\Delta T}_{on} - \overline{\Delta T}_{off})}$$

$F_R$ and $F_F$ can be averaged to obtain the averaged flow ($\overline{F}$) over one data collection cycle as shown in FIG. 6.

$$\overline{F} = \frac{F_R + F_F}{2}$$

A suitable calibration constant can be used to adjust the values of $F_R$, $F_F$ and $\overline{F}$.

Accordingly, by using two temperature sensors 19 and 20, cardiac output can be determined several times a minute in accordance with FIGS. 3–6, yielding an effectively continuous cardiac output value. Because such measurements can be made using relatively low power levels, the danger that the heart may be damaged by the introduction of thermal energy is substantially eliminated.

It will be apparent that the foregoing technique, which has been described in connection with the direct introduction of heat as an indicator agent and the measurement of temperature, can readily be performed by those skilled in the art by using indicator agents which affect the pH of the blood or change other blood parameters.

Figure 7A:
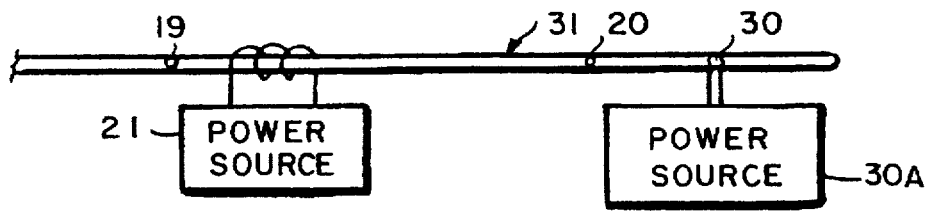
FIG. 7A shows a simplified diagrammatic view of another catheter used in the invention.
Figure 7B:
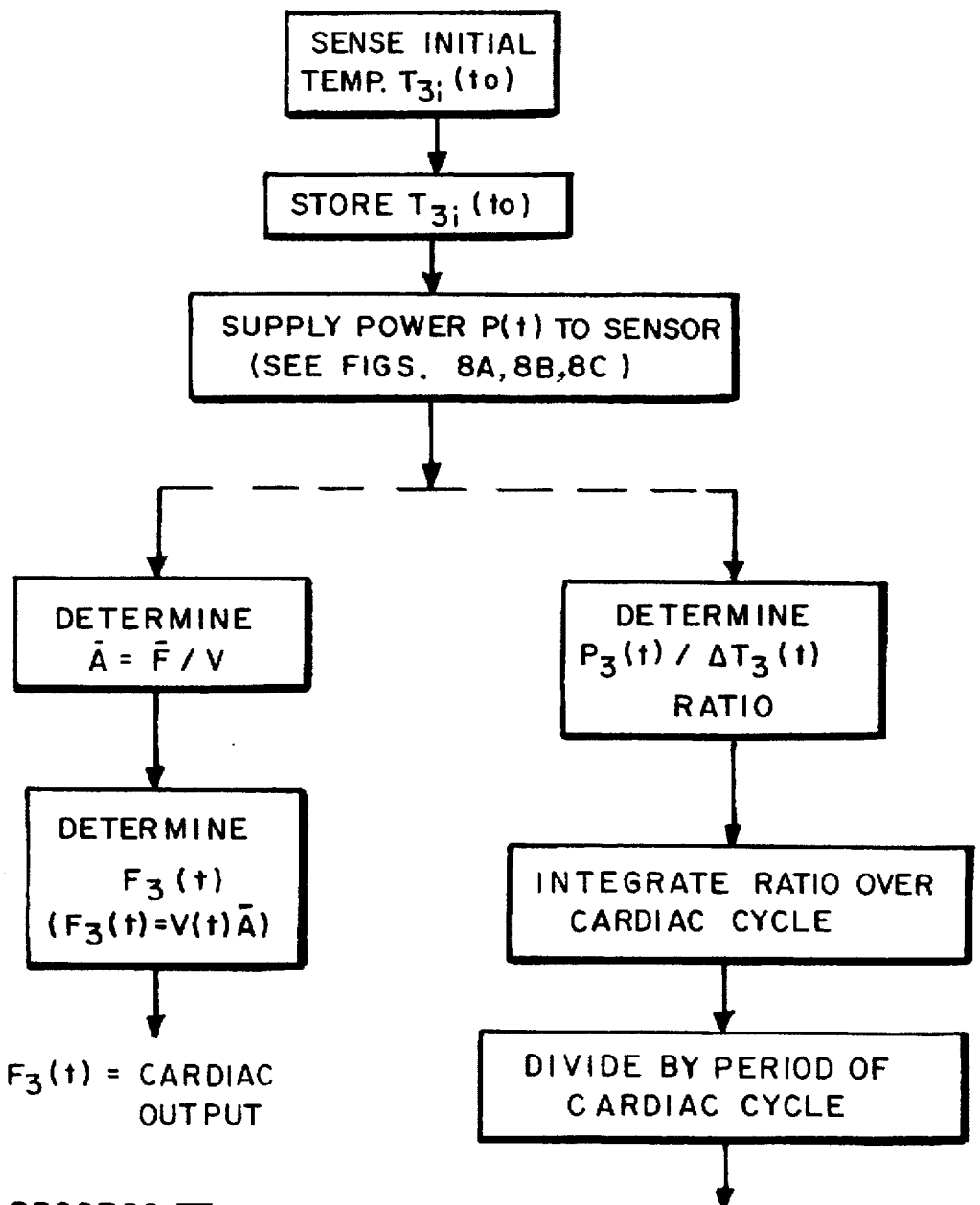
FIG. 7B shows a flow chart depicting steps in still another process of the invention.

In some situations it may be desirable to provide more frequent indications of cardiac output, such as, for example, the instantaneous cardiac output or the cardiac output averaged over each individual cardiac cycle (i.e. each heart beat). Such information can be provided using the further embodiments of the invention discussed below with reference to FIGS. 7–8. A single temperature sensor 30 at a location near the distal end of the catheter 31 (as shown in FIG. 7A) can be used to determine the instantaneous or beat-to-beat blood velocity V(t). The blood velocity can be combined with the cardiac output averaged over one or more data collection cycles to calculate instantaneous cardiac output. The process used is shown in the process depicted in FIG. 7B, identified as Process IV.

As seen therein, the initial temperature $T_{3i}(t)$ sensed at temperature sensor 30 as a function of time is smoothed, or filtered, in the manner as previously discussed above, and suitably measured and stored at an initial time $t_0$. A predetermined rise in temperature $\Delta T_3$ of the temperature sensor itself is selected. Power is then supplied at time $t_0$ to the temperature sensor 30 from a power source 30A connected thereto to cause its temperature $T_3(t)$ to rise by a predetermined amount.

Power may be supplied to the sensor in different ways according to the needs of the particular measurement and the relative simplicity or complexity of the required circuitry, three such ways being depicted in FIGS. 8A, 8B, and 8C.

For example, in a first mode of operation (FIG. 8A), heating power may be supplied to the sensor in such a manner as to keep the final sensor temperature $T_{3f}(t)$ constant at an initial level $\Delta T_3$ above the initial temperature $T_{3i}(t_0)$, i.e. $T_{3f}=T_{3i}(t_0)+\Delta T_3$ even when the local blood temperature varies with time, as illustrated in FIG. 9A. Under such conditions, the sensor is maintained at a time-varying temperature increment $\Delta T_3(t)$ above the instantaneous local blood temperature, $T_b(t)$.

Alternatively, in a second mode of operation, power can be supplied to the sensor so as to continuously maintain the sensor at a fixed temperature increment above the time varying local blood temperature, as illustrated in FIG. 9B. Under such conditions, $\Delta T_3(t)=\Delta T_3$, a constant, and the sensor temperature varies according to $T_{3f}(t)=\Delta T_3+T_{3i}(t)$.

A third mode of heating may also be convenient when the temperature sensors are temperature-sensitive resistors, or thermistors. Thus, when a thermistor is used, it may be more convenient to design an electrical heating circuit that maintains the sensor at a constant resistance increment above the resistance of the sensor that corresponds to the local blood temperature. If R is the corresponding resistance for a sensor temperature T, then these conditions are represented by $\Delta R_3(t)=\Delta R_3$, a constant, and the sensor resistance varies according to $R_{3f}(t)=\Delta R_3+R_{3i}(t)$, as illustrated in FIG. 9C. The change in temperature $\Delta T_3(t)$ is then replaced by the change in resistance $R_3(t)$ in the ratio which is integrated over a cardiac cycle. Further details and exemplary apparatus for such modes of operation are presented and described in U.S. Pat. No. 4,059,982, issued to H. F. Bowman on Nov. 29, 1977. With all three of the above approaches, power (P) is supplied to produce a temperature rise ($\Delta T$) both of which are then related to the instantaneous blood velocity and, hence, blood flow.

Techniques in which sensor heating power and temperature can be measured and used to provide more detailed information on cardiac output are described below. The technique involved can be applied to measure both instantaneous cardiac output, and the cardiac output for an individual cardiac cycle. Such detailed measurement information greatly enhances the diagnostic capability of a physician.

First, a method is described to measure instantaneous volumetric flow (which flow if measured at the location described above is the cardiac output). For each of the particular implementations described above, the power $P_3(t)$ applied to the temperature sensor 30 is controlled so as to maintain the final temperature of the sensor at a desired value $T_{3f}$. The power applied to the temperature sensor 30 or, more generally, the ratio of the power applied to the sensor to the temperature increment, $P_3(t)/\Delta T_3(t)$, is directly correlated with the fluid and flow properties of the flowing liquid about the sensor.

For example, the relationship between required sensor power and local fluid velocity, V(t), is given by a correlation of the form:

$$P(t)=4\pi k a \Delta T(t)[1+C_1 P_r{}^n(2a\rho V(t)/\mu)^m]$$

Where

P(t) instantaneous power to sensor k=thermal conductivity of fluid a=sensor radius $\Delta T(t)$=instantaneous temperature difference between heated sensor and unheated fluid temperature.

$C_1$=constant of calibration $P_r$=a non-dimensional "Prandtl" number which relates to the viscosity $\mu$, heat capacity Cp and thermal conductivity k of a fluid.

n,m=power factors which are determined from experimental data $\rho$=fluid density $\mu$=viscosity V(t)=instantaneous fluid velocity The fluid flow velocity in the vicinity of the sensor can be determined from the required sensor heating power. Volumetric flow in the vessel can then be determined with one further assumption for the distribution of the fluid flow within the vessel. For example, assuming a uniform velocity profile within the vessel, volumetric flow $F_3$ is given by $$F_3=V\,A$$

where V is the fluid velocity in the vessel and A is the flow area. If the fluid flow area A is not previously known, it may be inferred from the measurement of average volumetric flow in the vessel. Such average volumetric flow can be determined, for example, by using the techniques of the invention already described above herein or by using other techniques for yielding comparable information. For example, if F is the average cardiac output, typically measured over several cardiac cycles, as described above, and V is the average fluid velocity, determined by calculating an average value for the instantaneous flow velocity over at least one cardiac cycle, then one such estimate for the average flow area A is given by $$\bar{A} = \bar{F}/\bar{V}$$

Therefore, given the sensor measured heating power, first the fluid velocity and then volumetric flow can be calculated at any desired instant in time, i.e., $F_{3(t)} = V(t)\bar{A}$, yielding an instantaneous measure of volumetric flow, i.e., cardiac output.

In another embodiment, a method to measure cardiac output over a single cardiac cycle is described. As described above in different implementations, the power $P_3(t)$ applied to the temperature sensor 30 is controlled so as to maintain the temperature of the sensor at a desired signal value $T_3$. The power applied to the temperature sensor 30, or more generally, as discussed above, the ratio of the power applied to the sensor to the temperature increment, i.e., $P_3(t)/\Delta T_3(t)$, is directly correlated with the properties of the fluid flow in the vicinity of the sensor.

Thus, the integrated value of the power to temperature ratio over a single cardiac cycle is directly correlated with, i.e., is proportional to the average cardiac output over the cardiac cycle, $$\int_{\text{cardiac cycle}} \frac{P_3(t)}{\Delta T_3(t)} dt \propto \bar{F}$$

or, alternatively expressed $$\frac{1}{T} \int_{\text{cardiac cycle}} \frac{P_3(t)}{\Delta T_3(t)} dt \propto \bar{F}$$

where T represents the period of the cardiac cycle and $\bar{F}$ correspondingly represents cardiac output averaged over the cardiac cycle. Thus, the average cardiac output $\bar{F}$ over an individual cardiac cycle then can be determined from the measured and integrated power and temperature signals from the sensor.

Furthermore, an explicit correlation for integrated power and average cardiac output over the cardiac cycle may be dispensed with if a simple qualitative indication of the change in cardiac output on a cardiac cycle-to-cardiac cycle basis is desired. To obtain such information, a given measurement of cardiac output is taken as associated with a corresponding measured value of the integrated sensor signal over a cardiac cycle. The measurement of cardiac output could be obtained intermittently by the techniques described in this invention or other similar techniques. Since cardiac output is known to be correlated with the value of the integrated sensor signal over the cardiac cycle, any changes in the sensor signal indicate a corresponding change in cardiac output.

In certain situations, it may be desirable to compensate for temperature variations in the blood which is flowing past the sensor, as this may affect the value of F(t). A process for such compensation is depicted as Process IV in FIG. 7B wherein a temperature $T_2(t)$ is sensed by a second sensor (which may be, for example, sensor 19 or sensor 20) at a location remote from sensor 30 (see FIG. 7A). For example, knowledge of the instantaneous blood temperature is required for the process in which the heated sensor is maintained at a constant increment above the local blood temperature. In this case, the temperature $T_2(t)$ is used as a proxy for the temperature $T_3(t)$ which would be measured in the absence of sensor heating.

In a further alternative embodiment, where only two sensors 19 and 20 are utilized (as shown in FIG. 2), sensor 20 can be used as the primary sensor when calculating instantaneous cardiac output (equivalent to sensor 30 in FIG. 7A) and sensor 19 can be used as the secondary temperature compensation sensor. In such an embodiment, the averaged cardiac output can be determined using sensors 19 and 20, as set forth in FIGS. 3–6 and the instantaneous cardiac output can then subsequently be determined using sensors 19 and 20, as set forth in FIGS. 7B and either FIGS. 8A, 8B or 8C, such average and instantaneous cardiac output determinations being made in sequence by the microprocessor to provide the cardiac information in both forms, as desired.

As mentioned above, when using the above described catheter, the various flow values which are determined in accordance with the processes as discussed above are proportional to flow but may not be equal to the actual flow values unless they are suitably calibrated since the correspondence between the calculated and actual values depends on the manner in which a particular catheter is constructed and used. A calibration constant for a particular catheter can be represented by the slope and intercept of a curve which relates the calculated flow and the actual flow, in accordance with the following relationship:

$$F_{actual} = aF_{calc} + b$$

where, as illustrated in FIG. 10, "a" is the slope of a straight line 35 and "b" is the intercept thereof along the vertical axis. Curve 35 can be obtained by using a known catheter and known flow values therein to construct a curve 36. The best straight line fit is determined as line 35. The slope "a" and intercept "b" are thereby determined. Such determined values for "a" and "b" can be used with the calculated flow values in each case to determine the actual flow from the calculated flow.

While the above description discusses preferred embodiments of the invention, modifications thereof may occur to those in the art within the spirit and scope of the invention. Hence, the invention is not to be construed as limited to particular embodiments described, except as defined by the appended claims.

What is claimed is:

1. A method for determining blood flow in a living body comprising the steps of:
   changing the thermal energy level by a predetermined amount at a site in a blood flow path of said living body;
   detecting the temperatures at a first location upstream of said site and a second location downstream of said site;
   determining the temperature difference between said first and second locations at one energy level;
   determining the temperature difference between said first and second locations at the changed energy level; and
   calculating blood flow as a function of the change in energy level and of the temperature differences measured prior to and following the change in energy level.

2. A method in accordance with claim 1 wherein said first location is substantially thermally isolated from thermal energy changes occurring at said site.

3. A method in accordance with claim 2 wherein said blood flow path includes at least a portion of the heart of a living body and the blood flow represents cardiac output.

4. A method in accordance with claim 3 wherein said site is at least partially in the right atrium of the heart, said first location is in the vena cava of the heart, and the second location is in or near the pulmonary artery of the heart.

5. A method in accordance with claim 3 wherein said site is at least partially the right atrium of the heart, said first location is in the vena cava of the heart, and the second location is in or near the right ventricle of the heart.

6. A method in accordance with claims 1, 2, 3, 4, or 5, wherein said changing step comprises the step of applying thermal energy from a catheter borne thermal energy source which is positioned in the blood flow path, wherein temperatures are detected by temperature sensors in said catheter at said first and second locations, respectively.

7. A method for determining blood flow in a living body comprising the steps of:
changing the thermal energy at a site in a blood flow path of said living body, from a first level to a second level;
determining a characteristic of the temperature difference between the temperatures in said blood flow path at a first location upstream of said site and at a second location downstream of said site at said first level;
determining a characteristic of the temperature difference between the temperatures in said blood flow path at the first location and at the second location at said second level;
determining the difference between the characteristics of said temperature differences;
calculating blood flow as a function of the difference between the characteristics of said temperature differences and the change in thermal energy from said first level to said second level.

8. A method in accordance with claim 7, wherein said first and second determining steps each comprises the step of determining the characteristic over a specified time period and the third determining step repeats.

9. A method in accordance with claim 8 wherein each of said characteristics is the average of the temperature differences.

10. A method in accordance with claim 8 wherein the specified time period is at least one respiratory cycle.

11. A method in accordance with claim 7, 8, 9, or 10 wherein said blood flow path includes at least a portion of the heart of a living body where the blood flow represents cardiac output.

12. A method in accordance with claim 11 wherein said site is at least partially in the right atrium of the heart, said first location is in the vena cava of the heart, and the second location is in or near the pulmonary artery of the heart.

13. A method in accordance with claim 11 wherein said site is at least partially in the right atrium of the heart, said first location is in the vena cava of the heart, and the second location is in or near the right ventricle of the heart.

14. A method in accordance with claim 7 wherein each of said characteristic temperature difference determining steps includes the steps of:
detecting temperatures at said first location upstream of said site and at said second location downstream of said site during each cycle of one or more respiratory cycles, when said thermal energy is at said first level and when said thermal energy is at said second level;
determining temperature differences between said temperatures for each respiratory cycle, when said thermal energy is at said first level and when said thermal energy is at said second level; and
determining the average of said temperature differences over multiple respiratory cycles.

15. A method in accordance with claim 7 wherein:
said thermal energy level changing step includes applying a predetermined amount of power P at said site to change said thermal energy level from said first level to said second level and said cardiac output calculating step includes the steps of
calculating a rise-time cardiac output component as a function of the power P, the calculated average rise-time temperature difference, and the heat capacity of blood;
calculating a fall-time cardiac output component as a function of the power P, the calculated fall-time difference, and the heat capacity of blood; and
calculating the cardiac output as a function of the rise-time and fall-time cardiac components.

16. A method in accordance with claims 7, 8, 9 10 and 15 further comprising successively repeating the steps a plurality of times for repeatedly calculating the cardiac output to provide an effectively continuous calculations thereof.

17. A method in accordance with claim 16 further comprising averaging the repeated calculations over a selected number of said plurality of times to provide an averaged cardiac output over said selected number of times.

18. A method for determining blood flow in a living body comprising the steps of:
changing a value of a selected parameter of blood at a site in a blood flow path of said living body, from a first level to a second level;
determining the difference between the value of the selected parameter in said blood flow path at a first location upstream of said site and at a second location downstream of said site at said first level;
determining the difference between the value of the selected parameter in said blood flow path at the first location and at the second location at said second level;
determining the difference between the value obtained in the first said difference determining steps and the value obtained in the second said difference determining steps; and
calculating blood flow as a function of the difference between the values obtained in said first and second difference determining steps and the change in the value of the selected parameter from said first level to said second level.

19. A method in accordance with claim 18 wherein said blood flow path includes at least a portion of the heart of a living body where the blood flow represents cardiac output.

20. A method for determining blood flow in a living body comprising the steps of:
(a) changing the thermal energy of blood at a site in a blood flow path of the living body from an initial condition to a changed condition;
(b) determining a first difference in temperatures in the blood flow path at a first location relative to said site and at a second location downstream of said site when the thermal energy of blood at said site is at said initial condition;
(c) determining a second difference in temperatures in the blood flow path at the first location and at the second location when the thermal energy of blood at said site is at said changed condition;
(d) producing a signal functionally related to the change in said first and second temperature differences determined in said steps (b) and (c); and
(e) calculating blood flow as a function of the signal produced in step (d) and as a function of the change produced in step (a).

21. A method according to claim 20, wherein said first location is upstream of said site.

22. A method for determining blood flow in the blood flow path of a living body comprising the steps of:
   (a) repeatedly changing the thermal energy of blood at a site in the blood flow path between initial and changed conditions;
   (b) determining temperature differences in the blood flow path between a location upstream of said site and a location downstream of said site when the thermal energy of blood at said site is at the initial condition;
   (c) determining temperature differences in the blood flow path between said upstream location and said downstream location when the thermal energy of blood at said site is at the changed condition;
   (d) repeatedly calculating blood flow as a function of the temperature differences determined in steps (b) and (c) and the changes produced in step (a) to provide a substantially continuous blood flow calculation.

23. A method according to claim 22 further comprising:
   the step of determining the differences between the temperature differences determined in step (b) and the temperature differences determined in step (c); wherein said calculating step comprises calculating blood flow as a function of the changes produced in step (a) and said differences between the temperature differences determined in step (b) and the temperature differences determined in step (c).

24. A method according to claim 22, wherein the duration of each of the initial and changed conditions produced by said changing step includes one or more respiratory cycles.

25. A method for determining blood flow in the blood flow path of a living body comprising:
   changing a characteristic of blood at a site in the blood flow path;
   providing a first signal functionally related to the characteristic of blood in the blood flow path at a location downstream of said site;
   providing a second signal substantially unaffected by said changing step, corresponding to the characteristic of blood at a location in the blood flow path upstream of said site;
   determining differences between said first and second signals when one characteristic obtains;
   determining differences between said first and second signals when a changed characteristic obtains;
   ascertaining the differences between the differences determined by said determining steps;
   calculating blood flow as a function of the differences ascertained by said ascertaining step and the change introduced by said changing step.

26. A method according to claim 25, wherein the characteristic changed by said changing step is thermal energy.

27. A method according to claim 26, wherein the second signal providing step comprises the step of providing a signal functionally related to the thermal energy characteristic of blood in the blood flow path at a location upstream of said site.

28. A method for determining blood flow in the blood flow path of a living body comprising:
   changing a thermal energy characteristic of blood at a site in the blood flow path between a first condition and a second condition;
   providing a first signal functionally related to the change in the thermal energy characteristic of blood in the blood flow path produced by said changing step;
   providing a second signal representing the thermal energy characteristic of blood in the blood flow path substantially unaffected by said changing step; and
   calculating blood flow as a function of the difference in the value of said first and second signals during the first condition produced by said changing step, the difference in the value of said first and second signals during the second condition produced by said changing step, and the change in the thermal energy characteristic of blood introduced by said changing step.

29. A method according to claim 28, wherein said second signal is functionally related to the thermal energy characteristic of blood in the blood flow path at a location upstream of and substantially thermally isolated from said site.

30. A method for determining blood flow in the blood flow path of a living body comprising:
   supplying a known amount of indicator agent at a site in the blood flow path for producing a cycle of rising values and falling values associated with indicator agent in the blood flow path;
   detecting values associated with indicator agent in said blood flow path at a location downstream of said site thereby producing a signal having a value variable in accordance with variation in indicator agent at said downstream location;
   detecting values associated with indicator agent in said blood flow path at a location upstream of said site thereby producing a signal having a value variable in accordance with variation in indicator agent at said upstream location;
   determining differences in said signals produced at said upstream and downstream locations; and
   calculating blood flow as a function of the indicator agent supplied by said supplying step and the differences determined by said determining step.

31. A method according to claim 30 further comprising successively repeating the steps a plurality of times and calculating blood flow to effectively provide the continuous calculation thereof.

32. A method in accordance with claim 31 further comprising the step of averaging the repeated calculations over a selected number of said plurality of times to provide an averaged blood flow over said selected number of times.

33. A method in accordance with claims 31 or 32, wherein each repetition of the steps occurs over one or more respiratory cycles.

34. A method of determining blood flow in the blood flow path of a living body comprising:
   supplying a known amount of power at a site in the blood flow path for producing repeating temperature rises and temperature falls;
   detecting temperature in said blood flow path at a location downstream of said site;
   producing a downstream signal having a value variable in accordance with variation in the temperature detected at said downstream location;
   detecting temperature in said blood flow path at a location upstream of said site;
   producing an upstream signal having a value variable in accordance with variation in the temperature detected at said upstream location;
   determining differences between said upstream and downstream signals for each repetition of said temperature rises and temperature falls; and
   calculating blood flow as a function of the power supplied by said supplying step over a succession of repetitions of said pattern of temperature rises and temperature falls and differences determined by said determining step between upstream and downstream signals corresponding to said succession of repetitions.

35. A method for determining blood flow in the blood flow path of a living body comprising:

introducing a known amount of an agent at a site in the blood flow path to change values of a selected parameter of the blood;

detecting values of said parameter in said blood flow path at a first location downstream of said site;

detecting values of said parameter in said blood flow path at a second location upstream of said site;

determining the differences in the values detected at said first and second locations over intervals when the effect of introduction of agent is detectable at said first location and when the effect of introduction of agent is not substantially detectable at said first location; and calculating blood flow as a function of the amount of agent introduced by said introducing step, the differences in the values of the parameter detected at the first and second locations when the effect of introduction of agent is detectable at said first location, and the differences in the values of the parameter detected at the first and second locations when the effect of introduction of agent is not substantially detectable at said first location.

36. A method according to claim 35, wherein said agent is thermal energy and said parameter is temperature.

37. A method for determining blood flow in a living body comprising the steps of:

introducing a known thermal energy input into the blood flow path at a location between two thermal sensors spaced apart in said blood flow path;

determining temperature differences between said sensors over one or more respiratory cycles during the period when the blood temperature at the downstream sensor is changed by said introducing step;

determining temperature differences between said sensors over one or more respiratory cycles during the period when the blood temperature at the downstream sensor is not substantially changed by said introducing step, and calculating blood flow as a function of the thermal energy input, the temperature differences determined by the first said determining step and the temperature differences determined by the second said determining step.

38. A method according to claim 37, wherein said introducing step comprises introducing thermal energy between an upstream thermal sensor in the vena cava or right atrium of the heart of the living body and a down stream sensor in the right ventricle or pulmonary artery, whereby blood flow calculated represents cardiac output.

39. A method according to claims 37 or 38, wherein:

said introducing step comprises transmitting thermal energy to the blood stream during one or more respiratory cycles and, in one or more succeeding respiratory cycles, not transmitting a significant amount of thermal energy to said blood stream.

40. A method for determining blood flow in the blood flow path of a living body comprising the steps of:

introducing into a site in the blood flow path a factor to change a value of a selected parameter of blood;

determining a first signal as a function of the value of the parameter at a location downstream of said site as the value of said parameter changes at the downstream location as a result of the change introduced at said site by said changing step;

detecting the value of the selected parameter at a location in said blood flow path upstream of said site; and producing a signal proportional to blood flow as a function of said first signal, the value detected by said detecting step and the change introduced by said introducing step.

41. A method in accordance with claim 40, wherein said factor is thermal energy, said selected parameter is temperature and the first said determining step comprises the step of detecting temperature change at said downstream location.

42. A method in accordance with claim 41, wherein said detecting step comprises the step of detecting temperature at a location in said blood flow path upstream of said site.

43. A method for determining blood flow in the blood flow path of a living body comprising:

introducing a known amount of an indicator agent at a site in the blood flow path;

detecting values associated with indicator agent in the blood flow path at a first location downstream of said site during an interval including substantially the time from the start of introduction of the agent until the introduced agent has cleared the site;

detecting values associated with indicator agent in the blood flow path during said interval at a second location upstream of said site substantially isolated from the effects of indicator agent introduced by said introducing step;

determining a difference signal between values detected at said first and second locations during said interval; and calculating blood flow as a function of the amount of indicator agent introduced by said introducing step and the integral of said difference signal over said interval.

44. A method according to claim 43 wherein said agent is thermal energy and said value is temperature.

45. A method for determining blood flow in the blood flow path of a living body comprising:

(a) supplying a known amount of indicator agent at a site in the blood flow path for producing cycles of rising values and falling values associated with indicator agent in the blood flow path over an interval of one or more respiratory cycles in duration;

(b) detecting values associated with indicator agent in the blood flow path at a first location downstream of said site;

(c) detecting values associated with indicator agent in the blood flow path at a second location upstream of said site;

(d) determining differences between values detected at said first and second locations;

(e) detecting the effects of respiratory cycles on the output of step (d);

(f) processing the effects detected in step (e) to produce a processed signal; and (g) calculating blood flow as a function of the output of step (a) and the processed signal produced in step (f).

46. A method according to claim 45, wherein said processing step comprises the step of filtering the effects detected in step (e) out of the differences determined in step (d) to produce a filtered signal.

47. A method according to claim 46, wherein said supplying step occurs over a series of respiratory cycles and said filtering step comprises the steps of:

(a) recognizing the duration of each respiratory cycle in the series of respiratory cycles; and (b) obtaining an average value of the differences determined in step (d).

48. A claim according claims 45, 46 or 47, wherein said indicator agent is thermal energy and said values are temperature values.

49. A method for determining blood flow in the blood flow path of a living body comprising the steps of:

(a) supplying a known amount of indicator agent at a site in the blood flow path for producing repeating rising values and falling values associated with indicator agent in the blood flow path over an interval including a series of respiratory cycles;

(b) detecting values associated with indicator agent in the blood flow path at a location downstream of said site;

(c) providing second values substantially unaffected by step (a), corresponding to values associated with indicator agent in the blood flow path at a location upstream of said site;

(d) determining differences between the first said values and said second values;

(e) detecting the effects of respiratory cycles on said differences during said interval;

(f) processing the effects detected in step (e) to produce a processed signal; and (g) calculating blood flow as a function of the output of step (a) and the signal produced in step (f).

50. A claim according to claim 49, wherein said indicator agent is thermal energy and said values are temperature values.

51. A method according to claim 50, wherein said processing step comprises the step of filtering the effects detected in step (e) out of the differences determined in step (d) to produce a filtered signal.

52. A method according to claim 51, wherein said filtering step comprises the steps of:

(a) recognizing the duration of each respiratory cycle in the series of respiratory cycles; and (b) obtaining an average value of the differences determined in step (d) over each respiratory cycle.

53. A method according to claim 49 or 52, wherein the rising values and falling values produced by said supplying step are characterized by intervals of substantially equal duration alternating between a base value of indicator agent and values of indicator agent above the base value.

* * * * *

UNITED STATES PATENT AND TRADEMARK OFFICE
CERTIFICATE OF CORRECTION

PATENT NO. : 5,797,398
DATED : August 25, 1998
INVENTOR(S) : Bowman

It is certified that error appears in the above-identified patent and that said Letters Patent is hereby corrected as shown below:

At Column 14, line 48, insert --cycles of-- between "repeating" and "temperature"

At Column 14, line 62, insert --cycle of-- between "said" and "temperature"

At Column 14, line 66, change "pattern" to --cycle--

At Column 17, line 7, change "producing repeating rising" to --producing a repeating cycle of rising--

At Column 18, line 18, change "rising values" to --cycles of rising valves--

Signed and Sealed this

Twenty-second Day of June, 1999

Attest:

Q. TODD DICKINSON

*Attesting Officer*     *Acting Commissioner of Patents and Trademarks*